United States Patent
Bartáné Szalai et al.

(10) Patent No.: US 9,994,525 B2
(45) Date of Patent: Jun. 12, 2018

(54) H3 ANTAGONISTS CONTAINING PHENOXYPIPERIDINE CORE STRUCTURE

(71) Applicant: RICHTER GEDEON NYRT., Budapest (HU)

(72) Inventors: Gizella Bartáné Szalai, Budapest (HU); Gábor András Wágner, Budapest (HU); Béla Kiss, Budapest (HU); Éva Schmidt, Telki (HU); Ottília Balázs, Budapest (HU); Noémi Nagy, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 0 days. days.

(21) Appl. No.: 14/770,111

(22) PCT Filed: Mar. 6, 2014

(86) PCT No.: PCT/IB2014/059489
§ 371 (c)(1),
(2) Date: Aug. 25, 2015

(87) PCT Pub. No.: WO2014/136075
PCT Pub. Date: Sep. 12, 2014

(65) Prior Publication Data
US 2016/0009645 A1 Jan. 14, 2016

(30) Foreign Application Priority Data
Mar. 6, 2013 (HU) ..................... 1300139

(51) Int. Cl.
| | | |
|---|---|---|
| *C07D 211/46* | (2006.01) |
| *A61K 31/454* | (2006.01) |
| *C07D 401/12* | (2006.01) |
| *C07D 211/44* | (2006.01) |
| *A61K 45/06* | (2006.01) |
| *A61K 31/27* | (2006.01) |
| *A61K 31/445* | (2006.01) |
| *A61K 31/4545* | (2006.01) |
| *A61K 31/473* | (2006.01) |
| *A61K 31/55* | (2006.01) |
| *A61K 9/00* | (2006.01) |
| *A61K 9/02* | (2006.01) |
| *A61K 9/20* | (2006.01) |
| *A61K 9/48* | (2006.01) |

(52) U.S. Cl.
CPC .......... *C07D 211/46* (2013.01); *A61K 9/0019* (2013.01); *A61K 9/0095* (2013.01); *A61K 9/02* (2013.01); *A61K 9/2059* (2013.01); *A61K 9/4866* (2013.01); *A61K 31/27* (2013.01); *A61K 31/445* (2013.01); *A61K 31/454* (2013.01); *A61K 31/4545* (2013.01); *A61K 31/473* (2013.01); *A61K 31/55* (2013.01); *A61K 45/06* (2013.01); *C07D 211/44* (2013.01); *C07D 401/12* (2013.01)

(58) Field of Classification Search
None
See application file for complete search history.

(56) References Cited

U.S. PATENT DOCUMENTS

| | | |
|---|---|---|
| 2002/0040024 A1 | 4/2002 | Apodaca et al. |
| 2002/0065278 A1 | 5/2002 | Apodaca et al. |
| 2005/0222151 A1 | 10/2005 | Carruthers et al. |
| 2008/0139564 A1 | 6/2008 | Keith et al. |
| 2008/0280950 A1 | 11/2008 | Waterson et al. |
| 2008/0306046 A1 | 12/2008 | Ishii et al. |
| 2011/0021501 A1* | 1/2011 | Pouzet ................. C07D 519/00 514/213.01 |
| 2012/0022064 A1 | 1/2012 | Nakamura et al. |
| 2014/0135304 A1 | 5/2014 | Nirogi et al. |

FOREIGN PATENT DOCUMENTS

| | | |
|---|---|---|
| WO | WO 0212190 A2 * | 2/2002 |
| WO | WO 2008/064036 A1 * | 5/2008 |
| WO | WO 2009081197 A1 * | 7/2009 |

OTHER PUBLICATIONS

Freshney, RI. Culture of Animal Cells: A Manual of Basic Technique. John Wiley and Sons. 2005, 5th Ed., p. 8.*
Dermer, GB. Another Anniversary for the War on Cancer. Bio/Technology. 1994, vol. 12, p. 320.*
Cornelison, TL. Human papillomavirus genotype 16 vaccines for cervical cancer prophylaxis and treatment. Curr. Opin. Oncol. 2000, vol. 12(5), p. 466.*
West, AR. Solid State Chemistry and its Applications. John Wiley and Sons, Ltd. 1990, p. 358.*
Dandu, RR. et al. Synthesis and evaluation of a new series of 1'-cyclobutyl-6-(4-piperidyloxy)spiro[benzopyran-2,4'-piperidine] derivatives as high affinity and selective histamine-3 receptor (H3R) antagonists. Bioorganic & Medicinal Chemistry Letters. 2012, vol. 22, p. 2151.*

(Continued)

*Primary Examiner* — Taofiq A Solola
(74) *Attorney, Agent, or Firm* — Jason D. Voight (57) ABSTRACT

The present invention relates to new histamine $H_3$ ($H_3$) receptor subtype selective ligands of the general formula (I) and/or geometric isomers and/or stereoisomers and/or diastereomers and/or salts and/or hydrates and/or solvates thereof. The invention further relates to pharmaceutical compositions containing such compounds and the use of these compounds as medicaments for treatment and/or prevention of conditions which require modulation of $H_3$ receptors. The invention also cover the combinations of a compound of the general formula (I) and an acetylcholinesterase inhibitor.

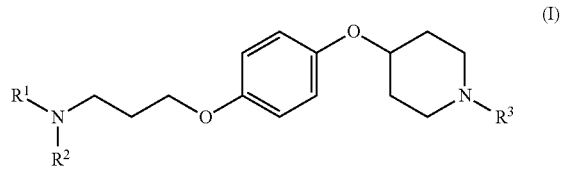

(I)

16 Claims, 2 Drawing Sheets

(56) References Cited

OTHER PUBLICATIONS

Ligneau, X. et al. Neurochemical and Behavioral Effects of Ciproxifan, A Potent Histamine H3-Receptor Antagonist. J. of Pharm. and Exp. Therap. 1998, vol. 287, p. 658.*

Brioni, JD. et al. Discovery of Histamine H3 Antagonists for the Treatment of Cognitive Disorders and Alzheimer's disease. J. of Pharm. and Exp. Therap. 2011, vol. 336, p. 38.*

Kuhne, S. et al. Several down, a few to go: histamine H3 receptor ligands making the final push towards the market. Expert Opinion on Investigational Drugs. 2011, vol. 20, p. 1629.*

Dvorak et al.: "4-Phenoxypiperidines: Potent, Conformationally Restricted, Non-Imidazole Histamine H3 Antagonist", J. Med. Chem., 2005, vol. 48, pp. 2229-2238.

Maslowska-Lipowicz et al.: "New 1-Benzyl-4-hydroxypiperidine Derivatives as Non-imidazole Histamine H3 Receptor Antagonists", Arch. Pharm. Chem. Life Sci., 2008, vol. 341, pp. 762-773.

Apodaca et al.: "A New Class of Diamine-Based Human Histamine H3 Receptor Antagonists: 4-(Aminoalkoxy) benzylamines", J. Med. Chem., 2003, vol. 46, pp. 3938-3944.

* cited by examiner

Histamine, prefrontal cortex

Histamine, hippocampus

Figure 1

Acetylcholine, prefrontal cortex

Acetylcholine, hippocampus

Figure 2

H3 ANTAGONISTS CONTAINING PHENOXYPIPERIDINE CORE STRUCTURE

This is the national stage of International Application PCT/IB2014/059489, filed Mar. 6, 2014.

FIELD OF THE INVENTION

The present invention relates to new histamine $H_3$ ($H_3$) receptor subtype selective ligands of the general formula (I) and/or geometric isomers and/or stereoisomers and/or diastereomers and/or salts and/or hydrates and/or solvates thereof. The invention further relates to pharmaceutical compositions containing such compounds and the use of these compounds as medicaments for treatment and/or prevention of conditions which require modulation of $H_3$ receptors. The invention also cover the combinations of a compound of the general formula (I) and an acetylcholinesterase inhibitor.

BACKGROUND OF THE INVENTION

It has long been known that histamine has a central role in the mediation of allergic reactions and it regulates gastric acid secretion. In the brain histamine regulates not only the basic homeostatic functions but higher brain functions as well such as learning and cognitive functions, sleep-wake cycle, food intake.

The histaminergic neurons originate from the tuberomamillary nucleus of the hypothalamus and send projections via the histaminergic path to most parts of the brain.

Histamine is an important biogenic amine involved in regulating physiological functions, the biological action of which is mediated via four receptors, named $H_1$, $H_2$, $H_3$ and $H_4$, their classification is based on their sequence differences, signaling properties and pharmacological profile (Haas and Panula, Nat Rev Neurosci (2003) 4:121-130; Leurs et al., Nat Rev Drug Discov (2005) 4:107-120; Esbenshade et al., Br J Pharmacol (2008) 154(6):1166-1181).

$H_1$ and $H_2$ receptors are known drug targets. The important role of $H_1$ receptors in allergic responses is well known, $H_1$ receptor antagonists are widely used. The main function of $H_2$ receptors is regulation of gastric acid secretion. The role of $H_4$ receptors has not been fully explored yet. According to preclinical evidences they can be involved in inflammatory processes and pain perception.

The histamine $H_3$ receptor controls the histamine synthesis and release as an autoreceptor (Arrang et al., Nature (1983) 302:832-837), and as a heteroreceptor has an essential role in the regulation of the release of acetylcholine and other neurotransmitters (noradrenaline, serotonin, dopamine) (Schlicker et al., Naunyn Schmiedebergs Arch Pharmacol (1988) 337:588-590; Schlicker et al., J Neural Transm Gen Sect (1993) 93:1-10; Schlicker et al., Naunyn Schmiedebergs Arch Pharmacol (1989) 340:633-638; Clapham and Kilpatrick, Br J Pharmacol (1992) 107:919-923; Blandina et al., Br J Pharmacol (1996) 119:1656-1664).

Histamine $H_3$ receptor antagonists/inverse agonists have a prominent role in the regulation of food intake and body-weight control via modulation of $H_3$ receptors functioning as auto and heteroreceptors (Passani et al., J Pharmacol Exp Ther (2011) 336, 24-29).

Histamine $H_3$ receptor antagonists evoke the synthesis and release of histamine and other monoamines in the brain. According to this mechanism they enhance wakefulness, improve cognitive functions, normalize vestibular reflexes. Histamine $H_3$ receptor inverse agonists increase the synaptic release of histamine, which enhance wakefulness via activation of postsynaptic $H_1$ receptors. The procognitive effect probably mediated not only via $H_3$ autoreceptors, but other transmitter systems regulated via $H_3$ heteroreceptors, such as cholinergic neurons, which play an important role in cognition, are also affected (Khateb et al., Neuroscience (1995) 69(2):495-506; Lin et al., J Neurosci (1996) 16(4):1523-1537; Passani et al., Trends Pharmacol Sci (2004) 25:618-625; Jones, Trends Pharmacol Sci (2005) 26:578-586; Bonaventure et al., Biochem Pharmacol (2007) 73:1084-1096; Ligneau et al., Biochem Pharmacol (2007) 73:1215-1224; Parmentier et al., Biochem Pharmacol (2007) 73:1157-1171; Haas et al., Physiol Rev (2008) 88:1183-1241).

Numerous $H_3$ inverse agonists or antagonists have been described (Berlin et al., J Med Chem (2011) 54:26-53; Łazewska et al., Expert Opin. Ther. Patents (2010) 20:1147-1169; Raddatz et al., Cur Top Med Chem (2010) 10:153-169) since histamine $H_3$ receptors were discovered (Arrang et al., Nature (1983) 302:832-837). Although several compounds have advanced to the clinical stage none of them gained therapeutic application, Phase 3 clinical trial has been started with only one compound, pitolisant (1-{3-[3-(4-chlorophenyl)propoxy]propyl}piperidine), in narcolepsy indication (Kuhne et al., Expert Opin Investig (2011) 20:1629-1648). The main drawbacks of the histamine $H_3$ receptor inverse agonist or antagonist compounds in getting a drug to the market were the following: (Łazewska et al., Expert Opin. Ther. Patents (2010) 20:1147-1169)

- Phospholipidosis: there are one or two basic nitrogens in the structure of histamine $H_3$ receptor inverse agonists or antagonists. Phospholipidosis is most probably caused by dibasic property, but in the case of monobasic compounds phospholipidosis can occur too (Ratcliffe Curr Med Chem (2009) 16:2816-2823). The dibasic JNJ-5207852 was rejected because it caused phospholipidosis (Bonaventure et al., Biochem Pharmacol (2007) 73:1084-1096).
- Cardiovascular side-effects, interaction with the hERG potassium channel: ABT-239 (Hancock, Biochem Pharmacol (2006) 71:1103-1113)
- High plasma protein binding: ABT-239 (Hancock, Biochem Pharmacol (2006) 71:1103-1113)
- Genotoxicity: A-331440 (Hancock et al., Basic Clin Pharmacol Toxicol (2004) 95:144-152)
- Poor pharmacokinetic characteristics: JNJ-5207852 (Bonaventure et al., Biochem Pharmacol (2007) 73:1084-1096). The spiro[benzopyrane-2,4'-piperidine]derivatives, which are structurally most closely related to compounds of our invention, but they have much less flexible structures, suffer from poor oral bioavailability therefore they should be further optimized. (Dandu et al., Bioorg Med Chem Lett (2012) 22:2151-2153)
- CYP enzyme interaction: NNC 38-1202 (Peschke et al., Bioorg Med Chem (2004) 12:2603-2616)

Elimination of the undesired properties from the potential histamine $H_3$ receptor inverse agonists or antagonists is not an easy task considering that although several histamine $H_3$ receptor inverse agonists or antagonists have undergone clinical investigation in different indications none of them was launched. (Kuhne et al., Expert Opin Investig (2011) 20:1629-1648)

The potential therapeutic application of histamine $H_3$ inverse agonists and antagonists includes a variety of indications such as treatment options of neurodegenerative diseases and cognitive deficits.

There are two main types of medication used for symptomatic treatments of Alzheimer's disease, which belongs to neurodegenerative diseases, one of them is the use of acetylcholinesterase enzyme inhibitor drugs (such as donepezil, rivastigmine, galantamine, tacrine) while the other is the use of an NMDA receptor antagonist (memantine). Clinical trials showed that the combined administration of acetylcholinesterase inhibitors and memantine did not outperform the monotherapies. The efficacy of the so far approved drugs used in the monotherapy is limited, they have only weak effect in terms of improvement of cognitive functions and this effect is limited to the first 6-12 months of therapy, moreover acetylcholinesterase inhibitors are effective only in 30-40% of the treated patients. Common side effects are nausea, vomiting, loss of appetite and more frequent defecation.

Improvement of cognitive dysfunction caused by Alzheimer's disease represents an important unmet medical need; there is a high demand for new drugs (Gerald and Ockert, Nat Rev Drug Discov (2013) 12(1):19-20.; Molino et al., (2013) Scientific World Journal 2013: 925702; McGleenon et al., (1999) Br J Clin Pharmacol 48(4):471-480).

The efficacy of acetylcholinesterase inhibitors has been tried to be improved by co-administration with drugs having different mechanism of action.

In recent clinical trials the co-administration of histamine $H_3$ inverse agonist or antagonist compounds with acetylcholinesterase inhibitors have been tried. In the case of three drug candidates there were no improvements on primary endpoints, therefore their further development was stopped (NCT01181310; Cho et al., Psychopharmacology (2011) 218(3):513-524; NCT 00420420; Egan et al., Curr Alzheimer Res (2012) 9(4):481-490; NCT01266525; Kirkesseli et al., J Nutr Health Aging (2013) 17(9):804).

The fact remains that there is no satisfactory monotherapy or combination therapy for the treatment of Alzheimer's disease.

SUMMARY OF THE INVENTION

Our aim was to synthesize structurally new, chemically variable, selective and drug-like $H_3$ antagonists and inverse agonists.

Surprisingly it was found, that the synthesized compounds containing phenoxy-piperidine core structure bind to the $H_3$ receptor with high affinity and selectivity, drug-like molecules, that is they have acceptable pharmacokinetic properties, for example their absorption is good, they can cross the blood brain barrier, they are devoid of cardiovascular side-effects, they do not cause phospholipidosis, they are not genotoxic and do not have interaction with CYP enzymes.

A number of diseases may be treated with histamine $H_3$ receptor ligands wherein the $H_3$ ligand can be antagonist or inverse agonist.

The histamine $H_3$ receptor antagonists and inverse agonists of the present invention and combinations of these compounds with acetylcholinesterase inhibitors are useful for treating cognitive dysfunctions associated with neurodegenerative disorders (such as Alzheimer's disease, Pick's disease) or age-related learning and mental disorders, or other cognitive disorders due to general medical conditions (such as attention-deficit hyperactivity disorder (ADHD) or Huntington disease), psychotic disorders (such as schizoaffective disorders or schizophrenia), sleep disorders (such as narcolepsy, hypersomnia, excessive day time sleeping (EDS)), eating disorders, obesity, obesity related metabolic disorders (such as hyperlipidemia, diabetes), dizziness and epilepsy.

Furthermore the histamine $H_3$ receptor antagonists and inverse agonists of the present invention and combinations of these compounds with acetylcholinesterase inhibitors are useful for treating anxiety disorders (such as generalized anxiety disorder, panic disorder, post traumatic stress disorder, or social anxiety disorder), mood disorders (such as depressed mood, adjustment disorder with depressed mood and anxiety), disturbances of the central nervous system (such as agitation or depression), and other central nervous system disorders (such as schizophrenia).

Furthermore the histamine $H_3$ receptor antagonists and inverse agonists of the present invention and combinations of these compounds with acetylcholinesterase inhibitors are useful for treating for example allergy, congestion (such as nasal congestion), hypotension, cardiovascular diseases, inflammatory pain, other pain induced disorders (such as neuropathic pain), alcohol abuse, irritable bowel syndrome and osteoarthritis.

The compounds of the present invention bind to the $H_3$ receptor with high affinity and selectivity (as compared to other histamine receptors, $H_1$, $H_2$ and $H_4$).

DETAILED DESCRIPTION OF THE INVENTION

The invention relates to compounds of the general formula (I)

(I)

wherein
  $R^1$, $R^2$ independently from each other represent hydrogen atom, or
  $C_1$-$C_6$ alkyl group, or
  $C_3$-$C_7$ cycloalkyl group, or
  $R^1$ and $R^2$ together with the adjacent basic nitrogen atom form a 4-10 membered, one or two ringed saturated heterocyclic group, which optionally contain one or two oxygen atom and/or sulfur atom and these heterocyclic groups are optionally substituted with one or two halogen atom, oxo group, $C_1$-$C_6$ alkyl group and the combination thereof;
  $R^3$ represents:
  hydrogen atom, —C(=O)$R^4$, —C(=O)—O$R^4$, —C(=O)—N$R^4R^5$ groups,
    wherein $R^4$ and $R^5$ independently from each other represent hydrogen atom, $C_1$-$C_6$ straight or branched alkyl group, or $C_3$-$C_7$ cycloalkyl group optionally substituted with $C_1$-$C_4$ alkyl group, and/or salts and/or stereoisomers and/or diastereomers and/or hydrates and/or solvates and/or polymorph modifications thereof.

The term "$C_1$-$C_6$ alkyl" as used herein refers to branched or straight chain alkyl groups comprising one to six carbon atoms.

The term "$C_3$-$C_7$ cycloalkyl" as used herein refers to carbocyclic groups comprising three to seven carbon atoms.

The term "halogen" as used herein alone or as a part of another group refers to fluorine, chlorine, bromine and iodine atom.

Both organic and inorganic acids can be used for the formation of acid addition salts. Suitable inorganic acids include, but not limited to, hydrochloric acid, sulfuric acid, nitric acid and phosphoric acid. Representatives of monovalent organic acids include, but are not limited to, formic acid, acetic acid, propionic acid, and different butanoic acids (butyric acids), valeric acid (pentanoic acid) and caproic acid (hexanoic acid). Representatives of bivalent organic acids include, but are not limited to, oxalic acid, malonic acid, maleic acid, fumaric acid and succinic acid. Other organic acids can also be used, such as hydroxy carboxylic acids, for example citric acid, tartaric acid, or aromatic carboxylic acids, for example benzoic acid or salicylic acid, as well as aliphatic and aromatic sulfonic acids, for example methanesulfonic acid, naphtalenesulfonic acid and p-toluenesulfonic acid.

A preferred group of acid addition salts are those in which the acid component itself is pharmaceutically acceptable and does not have a therapeutic effect in the applied dose and it does not have unfavourable influence on the effect of the active ingredient. These acid addition salts are pharmaceutically acceptable acid addition salts. Acid addition salts which are not pharmaceutically acceptable acid addition salts can be advantageous in the purification and/or isolation of the desired compounds of formula (I), and are therefore also included within the scope of the present invention.

Some compounds of the general formula (I)

(I)

wherein the meaning of $R^1$, $R^2$ and $R^3$ is as described above—can have geometric isomers, stereoisomer and/or diastereomer forms. These and the mixtures thereof are also included within the scope of the present invention.

Preferred compounds of the invention are those compounds of formula (I), wherein $R^1$ and $R^2$ together with the adjacent nitrogen atom form a 5-membered optionally substituted heterocyclic ring.

Further preferred compounds of the invention are those compounds of formula (I), wherein $R^1$ and $R^2$ together with the adjacent nitrogen atom form a 2-methyl-pyrrolidine ring.

Further preferred compounds of the invention are those compounds of formula (I), wherein $R^1$ and $R^2$ together with the adjacent nitrogen atom form a 2-(R)-methyl-pyrrolidine ring.

Further preferred compounds of the invention are those compounds of formula (I), wherein the meaning of $R^3$ is —C(=O)$R^4$, wherein the meaning of $R^4$ is $C_1$-$C_6$ straight or branched alkyl group, or $C_3$-$C_7$ cycloalkyl group optionally substituted with $C_1$-$C_4$ alkyl group.

Preferred compounds of the general formula (I) of the invention are the following compounds:
4-{4-[3-(piperidin-1-yl)-propoxy]-phenoxy}-piperidine-1-carboxylic acid tert-butyl ester
1-{3-[4-(piperidin-4-yl-oxy)-phenoxy]-propyl}-piperidine dihydrochloride salt
1-(4-{4-[3-(piperidin-1-yl)-propoxy]-phenoxy}-piperidin-1-yl)-ethanone hydrochloride salt
cyclobutyl-(4-{4-[3-(piperidin-1-yl)-propoxy]-phenoxy}-piperidin-1-yl)-methanone hydrochloride salt
(1-methyl-cyclopropyl)-(4-{4-[3-(piperidin-1-yl)-propoxy]-phenoxy}-piperidin-1-yl)-methanone hydrochloride salt
ethyl-4-{4-[3-(piperidin-1-yl)-propoxy]-phenoxy}-piperidine-1-carboxylate hydrochloride salt
N-ethyl-4-{4-[3-(piperidin-1-yl)-propoxy]-phenoxy}-piperidine-1-carboxamide
N-ethyl-N-methyl-4-{4-[3-(piperidin-1-yl)-propoxy]-phenoxy}-piperidine-1-carboxamide hydrochloride salt
4-(4-{3-[(2R)-2-methyl-pyrrolidin-1-yl]-propoxy}-phenoxy)-piperidine-1-carboxylic acid tert-butyl ester
4-(4-{3-[(2R)-2-methyl-pyrrolidin-1-yl]-propoxy}-phenoxy)-piperidine dihydrochloride salt
1-[4-(4-{3-[(2R)-2-methyl-pyrrolidin-1-yl]-propoxy}-phenoxy)-piperidin-1-yl]-ethanone hydrochloride salt
cyclobutyl-[4-(4-{3-[(2R)-2-methyl-pyrrolidin-1-yl]-propoxy}-phenoxy)-piperidin-1-yl]-methanone hydrochloride salt
(1-methyl-cyclopropyl)-[4-(4-{3-[(2R)-2-methyl-pyrrolidin-1-yl]-propoxy}-phenoxy)-piperidin-1-yl]-methanone hydrochloride salt
ethyl-4-(4-{3-[(2R)-2-methyl-pyrrolidin-1-yl]-propoxy}-phenoxy)-piperidine-1-carboxilate hydrochloride salt
N-ethyl-4-(4-{3-[(2R)-2-methyl-pyrrolidin-1-yl]-propoxy}-phenoxy)-piperidine-1-carboxamide
N-ethyl-N-methyl-4-(4-{3-[(2R)-2-methyl-pyrrolidin-1-yl]-propoxy}-phenoxy)-piperidine-1-carboxamide hydrochloride salt The invention also cover the combinations of a compound of the general formula (I) and an acetylcholinesterase inhibitor. The combinations of the present invention preferably contain donepezil, galantamine, tacrine or rivastigmine as acetylcholinesterase inhibitors.

Compounds of the general formula (I) of the invention can be synthesized according to the reaction scheme below (the meaning of groups is as described above for the formula (I), PG represents a protective group used for the protection of secondary amines)

Step A:

Intermediates of formula (II), preferably the compound containing tert-butoxycarbonyl protective group (Waterson et al., WO2006064218A1 (2006); Example 1 and 7; Ishii et al., EP1849773A1 (2007) Example 29), and intermediates of formula (III), preferably 1-chloro-3-(1-piperidinyl)-propane (Buchanan et al., Bioorg. Med. Chem. Let. (2011) 21:2394-2399; Sann et al., Tetrahedron (2007) 63:12903-12911) or (2R)-1-(3-chloropropyl)-2-methylpirrolidine (Nakamura et al., WO2010090347A1 (2010)) are reacted in an inert solvent, preferably in acetonitrile or N,N-dimethylformamide in the presence of organic or inorganic base, preferably $K_2CO_3$.

Step B

The protective group of intermediates of formula (IA) is cleaved. The preferably used tert-butoxycarbonyl protective group is cleaved with acid, preferably with hydrogen chloride absorbed in an organic solvent. Salt formation: the obtained compounds of formula (IB) are dissolved in a polar solvent, equimolar amount of acid is added and the solvent is removed by evaporation.

Step C

Intermediates of formula (IB) can be transformed into alkyl amines, carboxamides, carbamides or carbamates of formula (I) according to the following methods, and in given case salts are formed:

Step C1, carboxamides:
Intermediates of formula (IB) are reacted with the appropriate carboxylic acid in the presence of a coupling agent, or with the appropriate carboxylic acid chloride in the presence of a base in an inert solvent.

Step C2, carbamides:
Intermediates of formula (IB) are reacted with the appropriate carbamoyl chloride in the presence of a base in an inert solvent.

Step C3, carbamates:
Intermediates of formula (IB) are reacted with the appropriate carbonyl chloride in the presence of a base in an inert solvent.

Step C4, salt formation:
Compounds of formula (I) obtained in any of steps C1, C2, C3 are dissolved in a polar solvent, equimolar amount of acid is added and the solvent is removed by evaporation or the precipitated crystals are filtered off.

The present invention relates to pharmaceutical compositions comprising a therapeutically effective amount of a compound of formula (I) and/or geometric isomers and/or stereoisomers and/or diastereomers and/or salts and/or hydrates and/or solvates thereof and/or combinations of these compounds with acetylcholinesterase inhibitors and one or more pharmaceutically acceptable carrier(s).

The present invention preferably relates to pharmaceutical compositions comprising a therapeutically effective amount of a compound of formula (I) and/or geometric isomers and/or stereoisomers and/or diastereomers and/or salts and/or hydrates and/or solvates thereof and/or combinations of these compounds with acetylcholinesterase inhibitors and one or more pharmaceutically acceptable carrier(s) for the treatment and/or prevention of conditions which require the modulation of histamine $H_3$ receptors and/or strengthened modulation of the cholinergic system.

The pharmaceutical compositions of the present invention most preferably contain compounds of formula (I) with $H_3$ receptor antagonist or inverse agonist effect and/or geometric isomers and/or stereoisomers and/or diastereomers and/or salts and/or hydrates and/or solvates thereof and/or combinations of these compounds with acetylcholinesterase inhibitors.

The present invention also relates to pharmaceutical compositions containing a compound of formula (I) and/or geometric isomers and/or stereoisomers and/or diastereomers and/or salts and/or hydrates and/or solvates thereof and/or combinations of these compounds with acetylcholinesterase inhibitors, which would be effective in the treatment and/or prevention of age-related cognitive dysfunctions, learning and mental disorders (such as Alzheimer's disease, Pick's disease) or other cognitive disorders due to general medical conditions (such as attention-deficit hyperactivity disorder (ADHD) or Huntington disease), psychotic disorders (such as schizoaffective disorders or schizophrenia), sleep disorders (such as narcolepsy, hypersomnia, excessive day time sleeping (EDS)), eating disorders, obesity, obesity related metabolic disorders (such as hyperlipidemia, diabetes), dizziness, epilepsy, anxiety disorders (such as generalized anxiety disorder, panic disorder, post traumatic stress disorder or social anxiety disorder), mood disorders (such as depressed mood, adjustment disorder with depressed mood and anxiety), disturbances of the central nervous system (such as agitation or depression), other central nervous system disorders (such as schizophrenia), allergy, congestion (such as nasal congestion), hypotension, cardiovascular diseases, inflammatory pain, other pain induced disorders (such as neuropathic pain) alcohol-abuse, irritable bowel syndrome and osteoarthritis.

The present invention also relates to the use of a compound of formula (I) and/or geometric isomers and/or stereoisomers and/or diastereomers and/or salts and/or hydrates and/or solvates thereof and/or combinations of these compounds with acetylcholinesterase inhibitors for the manufacture of a medicament.

The present invention also provides the use of a compound of formula (I) and/or geometric isomers and/or stereoisomers and/or diastereomers and/or salts and/or hydrates and/or solvates thereof and/or combinations of these compounds with acetylcholinesterase inhibitors for the manufacture of a medicament for the treatment and/or prevention of age-related cognitive dysfunctions, learning and mental disorders (such as Alzheimer's disease, Pick's disease) or other cognitive disorders due to general medical conditions (such as attention-deficit hyperactivity disorder (ADHD) or Huntington disease), psychotic disorders (such as schizoaffective disorders or schizophrenia), sleep disorders (such as narcolepsy, hypersomnia, excessive day time sleeping (EDS)), eating disorders, obesity, obesity related metabolic disorders (such as hyperlipidemia, diabetes), dizziness, epilepsy, anxiety disorders (such as generalized anxiety disorder, panic disorder, post traumatic stress disorder or social anxiety disorder), mood disorders (such as depressed mood, adjustment disorder with depressed mood and anxiety), disturbances of the central nervous system (such as agitation or depression), other central nervous system disorders (such as schizophrenia), allergy, congestion (such as nasal congestion), hypotension, cardiovascular diseases, inflammatory pain, other pain induced disorders (such as neuropathic pain) alcohol-abuse, irritable bowel syndrome and osteoarthritis.

The present invention also provides a method for treating and/or preventing conditions which require modulation of histamine $H_3$ receptor functions comprising the administration to a mammal—including human—to be treated an effective amount of a compound of formula (I) and/or geometric isomers and/or stereoisomers and/or diastereomers and/or salts and/or hydrates and/or solvates thereof as such or as pharmaceutical composition.

The present invention also provides a method for treating and/or preventing conditions which require modulation of histamine $H_3$ receptor functions, such as age-related cognitive dysfunctions, learning and mental disorders (such as Alzheimer's disease, Pick's disease) or other cognitive disorders due to general medical conditions (such as attention-deficit hyperactivity disorder (ADHD) or Huntington disease), psychotic disorders (such as schizoaffective disorders or schizophrenia), sleep disorders (such as narcolepsy, hypersomnia, excessive day time sleeping (EDS)), eating disorders, obesity, obesity related metabolic disorders (such as hyperlipidemia, diabetes), dizziness, epilepsy, anxiety disorders (such as generalized anxiety disorder, panic disorder, post traumatic stress disorder or social anxiety disorder), mood disorders (such as depressed mood, adjustment disorder with depressed mood and anxiety), disturbances of the central nervous system (such as agitation or depression), other central nervous system disorders (such as schizophrenia), allergy, congestion (such as nasal congestion), hypotension, cardiovascular diseases, inflammatory pain, other pain induced disorders (such as neuropathic pain) alcohol-abuse, irritable bowel syndrome and osteoarthritis, comprising the administration to a subject to be treated an effective amount of a compound of formula (I) and/or geometric isomers and/or stereoisomers and/or diastereomers and/or salts and/or hydrates and/or solvates thereof as such or as pharmaceutical composition.

Compounds of formula (I) of the present invention and/or geometric isomers and/or stereoisomers and/or diastereomers and/or salts and/or hydrates and/or solvates thereof may be administered by any convenient method, for example by oral, parenteral, buccal, sublingual, nasal, rectal or transdermal administration.

The combinations of the compounds of general formula (I) and acetylcholinesterase inhibitors can also be administered by variety of routes and dosage forms. The active ingredients of the combinations can be formulated into a pharmaceutical composition either in combination or separately and the compositions can be administered in either single or multiple doses. The combinations of the compounds of general formula (I) and acetylcholinesterase inhibitors are administered simultaneously or subsequently.

The combinations of the present invention preferably contain donepezil, galantamine, tacrine or rivastigmine as acetylcholinesterase inhibitors.

The pharmaceutical compositions of the present invention for oral administration can be in liquid or solid form, for example syrups, suspensions or emulsions, tablets, film-tablets, dragees and capsules.

Suspensions or liquid compositions can contain the active ingredient in a suitable liquid carrier for example in an aqueous solvent, such as water, ethanol or glycerol, or in a non-aqueous solvent, such as polyethylene glycol or an oil. The formulation may also contain one or more suspending agent, preservative, flavoring and coloring agent or combinations thereof.

Compositions in the solid form of tablets can be manufactured using any suitable pharmaceutical carrier routinely used for preparing solid formulations. Examples of such carriers include magnesium stearate, starch, lactose, sucrose, cellulose, etc.

Compositions in the solid form of capsules can be manufactured using routine encapsulation procedures. For example pellets containing the active ingredient are prepared using standard carriers and then filled into a hard gelatine capsule; alternatively a dispersion or suspension is prepared using any suitable pharmaceutical carrier(s), such as aqueous gums, celluloses, silicates or oils and the obtained dispersion or suspension then filled into a soft gelatine capsule.

Compositions for parenteral administration can be formulated in the form of liquids or suspension, which contain besides the compounds of formula (I) of the present invention sterile aqueous carrier or parenterally acceptable oil, for example polyethylene glycol, polyvinyl pyrrolidine, lecithin, arachis oil or sesame oil. Alternatively the obtained solution can be lyophilized and the lyophilisate is redissolved with a suitable solvent just prior to administration.

Compositions for nasal administration can be formulated in the form of aerosols, drops, gels and powders. Compounds of the present invention for buccal or sublingual administration can be manufactured in the form tablets, lozenges and pastilles, wherein the active ingredient is formulated with a carrier, such as sugar and acacia gum, tragacanth or gelatine and glycerol etc.

Compositions for rectal administration can conveniently be formulated in the form of suppositories containing a commonly used suppository ingredient, such as cocoa butter.

Compositions for transdermal administration include ointments, gels and patches.

The above described ingredients and different routes of administration are merely representative. Other materials as well as processing techniques well known in the art can also be used.

The pharmaceutically acceptable compounds of formula (I) of the present invention—wherein the meaning of $R^1$ and $R^2$ is as described above—and/or geometric isomers and/or stereoisomers and/or diastereomers and/or pharmaceutically acceptable salts and/or hydrates and/or solvates thereof can normally be administered in a daily dosage regimen (for an adult patient) 1 to 4 times per day in case of all type of compositions, wherein each dosage unit may contain 0.05 (or preferably 0.005) to 2000 mg of a compound of formula (I) calculated as the free base. The compounds of the present invention can suitably administered for a period of continuous therapy, for example for a week or more.

EXAMPLES

The present invention is illustrated by the following not limiting examples.

The structures of all intermediates and final products were determined by NMR and mass spectroscopy.

Example 1

4-{4-[3-(piperidin-1-yl)-propoxy]-phenoxy}-piperidine-1-carboxylic acid tert-butyl ester A mixture of 4.2 g (14.3 mmol) of 4-(4-hydroxyphenoxy)piperidine-1-carboxylic acid tert-butyl ester, 3.7 g (18.7 mmol) of N-(3-chloropropyl)-piperidine and 5.9 g (42.9 mmol) of $K_2CO_3$ in 50 ml of N,N-dimethylformamide was stirred at 50° C. under nitrogen for 16 h. After cooling to room temperature the precipitated solid material was filtered off, washed with acetonitrile and the filtrate was concentrated in vacuum. The residue was purified by column chromatography using 100 g of silica gel and a mixture of ethyl acetate:ethanol=9:1 as eluent to yield 3.15 g (53%) of the title compound as crystalline material.

$^1$HNMR (400 MHz, DMSO-d6): 1.40 s (9H, $H_3$-18, $H_3$-18', $H_3$-18"); 2.31 br (4H, $H_2$-2, $H_2$-2'); 3.15 t br (2H, $H_{ax}$-14, $H_{ax}$-14'); 3.91 t (2H, $H_2$-7) 4.38 tt (1H, H-12); 6.82 m (2H, H-9, H-9'); 6.89 m (2H, H-10, H-10')

$^{13}$CNMR (100 MHz, DMSO-d6): 28.0 (C-18, C-18', C-18"); 40.9 (C-14, C-14'); 54.3 (C-2, C-2'); 66.4 (C-7); 72.8 (C-12); 115.3 (C-9, C-9'); 117.4 (C-10, C-10')

MS: m/z: [M+H]$^+$=419

Example 2

1-{3-[4-(piperidin-4-yl-oxy)-phenoxy]-propyl}-piperidine dihydrochloride salt To a stirred solution of 2.5 g (6 mmol) of 4-{4-[3-(piperidin-1-yl)-propoxy]-phenoxy}-piperidine-1 carboxylic acid tert-butyl ester (Example 1) in 20 ml of ethyl acetate 25 ml of ethyl acetate containing 21 w/w % of hydrogen chloride was added keeping the temperature below 10° C. The mixture was left to warm to room temperature and stirred at this temperature for 16 h. The precipitated crystals were filtered off and successively washed with ethyl acetate and diethyl ether to yield 2.16 g (92%) of the title compound as crystalline material.

$^1$HNMR (500 MHz, DMSO-d6): 2.80 br (2H, $H_x$-2, $H_x$-2'); 3.03 ddd (2H, $H_x$-14, $H_x$-14'); 3.99 t (2H, $H_2$-7); 4.51 tt (1H, H-12); 6.88 m (2H, H-9, H-9'); 6.95 m (2H, H-10, H-10'); 9.14 br (2H, $NH_2^+$-15); 10.50 br (1H, $NH^+$-1)

$^{13}$CNMR (125 MHz, DMSO-d6): 40.3 (C-14, C-14'); 52.0 (C-2, C-2'); 65.5 (C-7); 69.8 (C-12); 115.5 (C-9, C-9'); 117.4 (C-10, C-10')

MS: m/z: M$^{·+}$=318

Example 3

1-(4-{4-[3-(piperidin-1-yl)-propoxy]-phenoxy}-piperidin-1-yl)-ethanone hydrochloride salt To an ice-cooled solution of 0.39 g (1 mmol) of 1-{3-[4-(piperidin-4-yl-oxy)-phenoxy]-propyl}-piperidine dihydrochloride salt (Example 2) in 20 ml of dichloromethane 0.56 ml (4 mmol) of triethylamine was added, the mixture was stirred for 20 min and 0.11 ml (1.5 mmol) of acetyl chloride was added dropwise. The reaction mixture was stirred at room temperature for 16 h, then washed with 20 ml of 8 w/w % aqueous $NaHCO_3$ solution, the aqueous phase was extracted with 20 ml of dichloromethane and the combined organic phases were washed with 20 ml of water, dried over $Na_2SO_4$, filtered and concentrated. The crude product was dissolved in 10 ml of ethyl acetate and 10 ml of ethyl acetate containing 21 w/w % of hydrogen chloride was added, the precipitated crystals were filtered off, successively washed with ethyl acetate and diethyl ether to yield 0.33 g (83%) of the title compound as crystalline material.

$^1$HNMR (500 MHz, DMSO-d6): 2.01 s (3H, $H_3$-17); 3.43 d (2H, $H_{eq}$-2, $H_{eq}$-2'); 3.98 t (2H, $H_2$-7); 4.46 tt (1H, H-12); 6.87 m (2H, H-9, H-9'); 10.47 br (1H, $NH^+$-1)

$^{13}$CNMR (125 MHz, DMSO-d6): 21.2 (C-17); 52.1 (C-2, C-2'); 65.4 (C-7); 72.6 (C-12); 115.5 (C-9, C-9')

MS: m/z: M$^{·+}$=360

Example 4

Cyclobutyl-(4-{4-[3-(piperidin-1-yl)-propoxy]-phenoxy}-piperidin-1-yl)-methanone hydrochloride salt To an ice-cooled solution of 0.39 g (1 mmol) of 1-{3-[4-(piperidin-4-yl-oxy)-phenoxy]-propyl}-piperidine dihydrochloride salt (Example 2) in 20 ml of dichloromethane 0.56 ml (4 mmol) of triethylamine was added, the mixture was stirred for 20 min and 0.17 ml (1.5 mmol) of cyclobutyl carboxylic acid chloride was added dropwise. The reaction mixture was stirred at room temperature for 16 h, then washed with 20 ml of 8 w/w % aqueous $NaHCO_3$ solution, the aqueous phase was extracted with 20 ml of dichloromethane and the combined organic phases were washed with 20 ml of water, dried over $Na_2SO_4$, filtered and concentrated. The crude product was dissolved in 10 ml of ethyl acetate and 10 ml of ethyl acetate containing 21 w/w % of hydrogen chloride was added, the precipitated crystals were filtered off, successively washed with ethyl acetate and diethyl ether to yield 0.28 g (64%) of the title compound as crystalline material.

$^1$HNMR (500 MHz, DMSO-d6): 1.71 m (2H, $H_x$-4, $H_x$-19); 3.34 m (1H, H-17); 3.43 d (2H, $H_{eq}$-2, $H_{eq}$-2'); 3.98 t (2H, $H_2$-7); 4.45 tt (1H, H-12); 6.86 m (2H, H-9, H-9'); 10.32 br (1H, $NH^+$-1)

$^{13}$CNMR (125 MHz, DMSO-d6): 36.4 (C-17); 52.0 (C-2, C-2'); 65.4 (C-7); 72.6 (C-12); 115.4 (C-9, C-9'); 171.8 (C-16)

MS: m/z: [M+H]$^+$=401

Example 5

(1-methyl-cyclopropyl)-(4-{4-[3-(piperidin-1-yl)-propoxy]-phenoxy}-piperidin-1-yl)-methanon hydrochloride salt To an ice-cooled solution of 0.39 g (1 mmol) of 1-{3-[4-(piperidin-4-yl-oxy)-phenoxy]-propyl}-piperidine dihydrochloride salt (Example 2) in 10 ml of N,N-dimethylformamide 0.46 ml (3.25 mmol) of triethylamine was added, the mixture was stirred for 10 min, then 0.48 g (1.25 mmol) of HBTU and 0.13 g (1.25 mmol) of 1-methyl-cyclopropane-carboxylic acid were added. The reaction mixture was stirred at room temperature for 16 h, then 15 ml of 8 w/w % aqueous $NaHCO_3$ solution was added, the mixture was extracted with 3×8 ml of dichloromethane and the combined organic phases were washed with 10 ml of water, dried over $Na_2SO_4$, filtered and concentrated. The residue was purified by column chromatography using 15 g of silica gel and a mixture of ethyl acetate:ethanol=1:1 as eluent. The purified basic form of the title compound was dissolved in 10 ml of ethyl acetate and 5 ml of ethyl acetate containing 21 w/w % of hydrogen chloride was added, the precipitated crystals were filtered off, successively washed with ethyl acetate and diethyl ether to yield 0.23 g (53%) of the title compound as crystalline material.

$^1$HNMR (400 MHz, DMSO-d6): 0.53 m (2H, $H_x$-18, $H_x$-18'); 0.78 m (2H, $H_y$-18, $H_y$-18'); 1.22 s (3H, $H_3$-19);

1.40 m (1H, $H_x$-4); 2.86 br (4H, $H_{eq}$-2, $H_{eq}$-2'); 3.98 t (2H, $H_2$-7); 4.47 tt (1H, H-12); 6.86 m (2H, H-9, H-9'); 10.06 br (1H, $NH^+$-1)

MS: m/z: $[M+H]^+$=401

Example 6

Ethyl-4-{4-[3-(piperidin-1-yl)-propoxy]-phenoxy}-piperidine-1-carboxylate hydrochloride salt To an ice-cooled solution of 0.39 g (1 mmol) of 1-{3-[4-(piperidin-4-yl-oxy)-phenoxy]-propyl}-piperidine dihydrochloride salt (Example 2) in 20 ml of dichloromethane 0.56 ml (4 mmol) of triethylamine was added, the mixture was stirred for 10 min and 0.14 ml (1.5 mmol) of ethyl chloroformate was added dropwise. The reaction mixture was stirred at room temperature for 16 h, then washed with 3×20 ml of water, the organic phase was dried over $Na_2SO_4$, filtered and concentrated. The crude product was dissolved in 10 ml of ethyl acetate and 4 ml of ethyl acetate containing 21 w/w % of hydrogen chloride was added, the precipitated crystals were filtered off, successively washed with ethyl acetate and diethyl ether to yield 0.34 g (80%) of the title compound as crystalline material.

$^1$HNMR (400 MHz, DMSO-d6): 1.18 t (3H, $H_3$-18); 1.40 m (1H, $H_{ax}$-4); 2.88 q br (2H, $H_{ax}$-2, $H_{ax}$-2'); 3.99 t (2H, $H_2$-7); 4.04 q (2H, $H_2$-17); 4.43 tt (1H, H-12); 6.87 m (2H, H-9, H-9'); 10.04 br (1H, $NH^+$-1)

MS: m/z: $M^{·+}$=390

Example 7

N-ethyl-4-{4-[3-(piperidin-1-yl)-propoxy]-phenoxy}-piperidine-1-carboxamide

To an ice-cooled solution of 0.39 g (1 mmol) of 1-{3-[4-(piperidin-4-yl-oxy)-phenoxy]-propyl}-piperidine dihydrochloride salt (Example 2) in 20 ml of dichloromethane 0.35 ml (2.5 mmol) of triethylamine was added, the mixture was stirred for 10 min and 0.12 ml (1.5 mmol) of ethyl isocyanate was added dropwise. The reaction mixture was stirred at room temperature for 16 h, then washed with 3×20 ml of water, the organic phase was dried over $Na_2SO_4$, filtered and concentrated to yield 0.28 g (72%) of the title compound as crystalline material.

$^1$HNMR (400 MHz, DMSO-d6): 1.00 t (3H, $H_3$-19); 1.37 m (2H, $H_2$-4); 2.31 br (4H, $H_2$-2, $H_2$-2'); 3.91 t (2H, $H_2$-7); 4.36 tt (1H, H-12); 6.47 t (1H, NH-17); 6.82 m (2H, H-9, H-9')

MS: m/z: $M^{·+}$=389

Example 8

N-ethyl-N-methyl-4-{4-[3-(piperidin-1-yl)-propoxy]-phenoxy}-piperidine-1-carboxamide hydrochloride salt To an ice-cooled solution of 0.39 g (1 mmol) of 1-{3-[4-(piperidin-4-yl-oxy)-phenoxy]-propyl}-piperidine dihydrochloride salt (Example 2) in 20 ml of dichloromethane 0.35 ml (2.5 mmol) of triethylamine was added, the mixture was stirred for 10 min and 0.18 g (1.5 mmol) of methyl ethyl isocyanate was added dropwise. The reaction mixture was stirred at room temperature for 16 h, then washed with 3×20 ml of water, the organic phase was dried over $Na_2SO_4$, filtered and concentrated. The crude product was dissolved in 15 ml of ethyl acetate and 8 ml of ethyl acetate containing 21 w/w % of hydrogen chloride was added, the mixture was concentrated and the residue was triturated with diethyl ether to yield 0.34 g (77%) of the title compound as crystalline material.

$^1$HNMR (800 MHz, DMSO-d6): 1.05 t (3H, $H_3$-19); 1.37 m (2H, $H_2$-4); 2.72 s (3H, $H_3$-17); 2.87 q br (2H, $H_{ax}$-2, $H_{ax}$-2'); 3.10 q (2H, $H_2$-18); 3.98 t (2H, $H_2$-7); 4.39 tt (1H, H-12); 6.86 m (2H, H-9, H-9')

MS: m/z: $M^{·+}$=403

Example 9

4-(4-{3-[(2R)-2-methyl-pyrrolidin-1-yl]-propoxy}-phenoxy)-piperidine-1-carboxylic acid tert-butyl ester A mixture of 4.3 g (14.7 mmol) of 4-(4-hydroxyphenoxy)piperidine-1-carboxylic acid tert-butyl ester, 3.1 g (19.1 mmol) of (2R)-1-(3-chloropropyl)-2-methylpyrrolidine, 5.3 g (38.2 mmol) of $K_2CO_3$ and 50 ml of N,N-dimethylformamide was stirred under nitrogen for 16 h at 50° C. The reaction mixture was cooled to room temperature, the precipitated solid material was filtered, washed with acetonitrile and the filtrate was concentrated in vacuum. The residue was purified by column chromatography using 100 g of silica gel and a mixture of ethyl acetate:ethanol=4:1 as eluent to yield 2.4 g (39%) of the title compound as crystalline material.

$^1$HNMR (400 MHz, DMSO-d6): 0.99 d (3H, $H_3$-6); 1.40 s (9H, $H_3$-20, $H_3$-20', $H_3$-20''); 2.24 sex (1H, H-5); 3.93 t (2H, $H_2$-9); 4.38 tt (1H, H-14); 6.83 m (2H, H-11, H-11')

MS: m/z: $M^{·+}$=418

Example 10

4-(4-{3-[(2R)-2-methyl-pyrrolidin-1-yl]-propoxy}-phenoxy)-piperidine dihydrochloride salt To a stirred solution of 2.3 g (5.5 mmol) of 4-(4-{3-[(2R)-2-methyl-pyrrolidin-1-yl]-propoxy}-phenoxy)-piperidine-1-carboxylic acid tert-butyl ester (Example 9) in 20 ml of ethyl acetate 25 ml of ethyl acetate containing 21 w/w % of hydrogen chloride was added keeping the temperature below 10° C. The mixture was left to warm to room temperature and stirred at this temperature for 16 h. The precipitated crystals were filtered off and successively washed with ethyl acetate and diethyl ether to yield 1.76 g (82%) of the title compound as crystalline material.

$^1$HNMR (400 MHz, DMSO-d6): 1.36 br (3H, $H_3$-6); 1.92 m (2H, $H_2$-3); 4.01 t (2H, $H_2$-9); 4.51 tt (1H, H-14); 6.89 m (2H, H-11, H-11'); 9.12 br (2H, $NH_2^+$-17); 10.52 br (1H, $NH^+$-1)

MS: m/z: $M^{·+}$=318

Example 11

1-[4-(4-{3-[(2R)-2-methyl-pyrrolidin-1-yl]-propoxy}-phenoxy)-piperidin-1-yl]-ethanone hydrochloride salt To an ice-cooled solution of 0.39 g (1 mmol) of 4-(4-{3-[(2R)-2-methyl-pyrrolidin-1-yl]-propoxy}-phenoxy)-piperidine dihydrochloride salt (Example 10) in 20 ml of dichloromethane 0.56 ml (4 mmol) of triethylamine was added, the mixture was stirred for 20 min and 0.11 ml (1.5 mmol) of acetyl chloride was added dropwise. The reaction mixture was stirred at room temperature for 16 h, then washed with 20 ml of 8 w/w % aqueous $NaHCO_3$ solution, the aqueous phase was extracted with 3×10 ml of dichloromethane and the combined organic phases were washed with 20 ml of water, dried over $Na_2SO_4$, filtered and concentrated. The crude product was dissolved in 10 ml of ethyl acetate and 5 ml of ethyl acetate containing 21 w/w % of hydrogen chloride was added, the precipitated crystals were filtered off, successively washed with ethyl acetate and diethyl ether to yield 0.37 g (82%) of the title compound as crystalline material.

$^1$HNMR (400 MHz, DMSO-d6): 1.39 d (3H, $H_3$-6); 2.01 s (3H, $H_3$-19); 4.01 t (2H, $H_2$-9); 4.46 tt (1H, H-14); 6.87 m (2H, H-11, H-11'); 10.37 br (1H, $NH^+$-1)

MS: m/z: $[M+H]^+$=361

Example 12 cyclobutyl-[4-(4-{3-[(2R)-2-methylpyrrolidin-1-yl]-propoxy}-phenoxy)-piperidin-1-yl]-methanone hydrochloride salt To an ice-cooled solution of 0.39 g (1 mmol) of 4-(4-{3-[(2R)-2-methyl-pyrrolidin-1-yl]-propoxy}-phenoxy)-piperidine dihydrochloride salt (Example 10) in 20 ml of dichloromethane 0.56 ml (4 mmol) of triethylamine was added, the mixture was stirred for 20 min and 0.17 ml (1.5 mmol) of cyclobutyl carboxylic acid chloride was added dropwise. The reaction mixture was stirred at room temperature for 16 h, then washed with 20 ml of 8 w/w % aqueous $NaHCO_3$ solution, the aqueous phase was extracted with 3×10 ml of dichloromethane and the combined organic phases were washed with 20 ml of water, dried over $Na_2SO_4$, filtered and concentrated. The crude product was dissolved in 10 ml of ethyl acetate and 5 ml of ethyl acetate containing 21 w/w % of hydrogen chloride was added, the precipitated crystals were filtered off, successively washed with ethyl acetate and diethyl ether to yield 0.17 g (39%) of the title compound as crystalline material.

$^1$HNMR (400 MHz, DMSO-d6): 1.36 br (3H, $H_3$-6); 1.73 m (1H, $H_x$-21); 2.09 m (2H, $H_x$-20, $H_x$-20'); 4.00 t (2H, $H_2$-9); 4.45 tt (1H, H-14); 6.87 m (2H, H-11, H-11'); 10.06 br (1H, $NH^+$-1)

MS: m/z: $M^{·+}$=400

Example 13

(1-methyl-cyclopropyl)-[4-(4-{3-[(2R)-2-methyl-pyrrolidin-1-yl]-propoxy}-phenoxy)-piperidin-1-yl]-methanone hydrochloride salt To an ice-cooled solution of 0.39 g (1 mmol) of 4-(4-{3-[(2R)-2-methyl-pyrrolidin-1-yl]-propoxy}-phenoxy)-piperidine dihydrochloride salt (Example 10) in 10 ml of N,N-dimethylformamide 0.46 ml (3.25 mmol) of triethylamine was added, the mixture was stirred for 10 min, then 0.48 g (1.25 mmol) of HBTU and 0.13 g (1.25 mmol) of 1-methyl-cyclopropane-carboxylic acid were added. The reaction mixture was stirred at room temperature for 16 h, then 20 ml of 8 w/w % aqueous $NaHCO_3$ solution was added, the mixture was extracted with 3×10 ml of dichloromethane and the combined organic phases were washed with 10 ml of water, dried over $Na_2SO_4$, filtered and concentrated. The residue was purified by column chromatography using 15 g of silica gel and a mixture of ethyl acetate:ethanol=1:1 as eluent. The purified basic form of the title compound was dissolved in 10 ml of ethyl acetate and 5 ml of ethyl acetate containing 21 w/w % of hydrogen chloride was added, the precipitated crystals were filtered off, successively washed with ethyl acetate and diethyl ether to yield 0.15 g (34%) of the title compound as crystalline material.

$^1$HNMR (400 MHz, DMSO-d6): 0.53 m (2H, $H_x$-20, $H_x$-20'); 0.79 m (2H, $H_y$-20, $H_y$-20'); 1.22 s (3H, $H_3$-21); 1.37 br (3H, $H_3$-6); 4.00 t (2H, $H_2$-9); 4.47 tt (1H, H-14); 6.88 m (2H, H-11, H-11'); 10.43 br (1H, $NH^+$-1)

MS: m/z: $M^{·+}$=400

Example 14 ethyl-4-(4-{3-[(2R)-2-methyl-pyrrolidin-1-yl]-propoxy}-phenoxy)-piperidine-1-carboxilate hydrochloride salt To an ice-cooled solution of 0.39 g (1 mmol) of 4-(4-{3-[(2R)-2-methyl-pyrrolidin-1-yl]-propoxy}-phenoxy)-piperidine dihydrochloride salt (Example 10) in 20 ml of dichloromethane 0.56 ml (4 mmol) of triethylamine was added, the mixture was stirred for 10 min and 0.14 ml (1.5 mmol) of ethyl chloroformate was added dropwise. The reaction mixture was stirred at room temperature for 16 h, then washed with 3×20 ml of water, the organic phase was dried over $Na_2SO_4$, filtered and concentrated. The crude product was dissolved in 10 ml of ethyl acetate and 4 ml of ethyl acetate containing 21 w/w % of hydrogen chloride was added, the precipitated crystals were filtered off, successively washed with ethyl acetate and diethyl ether to yield 0.32 g (75%) of the title compound as crystalline material.

$^1$HNMR (400 MHz, DMSO-d6): 1.18 t (3H, $H_3$-20); 1.38 d (3H, $H_3$-6); 4.01 m (2H, $H_2$-9); 4.04 q (2H, $H_2$-19); 4.43 tt (1H, H-14); 6.88 m (2H, H-11, H-11'); 9.98 br/10.43 br (1H, $NH^+$-1)

MS: m/z: $M^{·+}$=390

Example 15

N-ethyl-4-(4-{3-[(2R)-2-methyl-pyrrolidin-1-yl]-propoxy}-phenoxy)-piperidine-1-carboxamide To an ice-cooled solution of 0.39 g (1 mmol) of 4-(4-{3-[(2R)-2-methyl-pyrrolidin-1-yl]-propoxy}-phenoxy)-piperidine dihydrochloride salt (Example 10) in 20 ml of dichloromethane 0.35 ml (2.5 mmol) of triethylamine was added, the mixture was stirred for 10 min and 0.12 ml (1.5 mmol) of ethyl isocyanate was added dropwise. The reaction mixture was stirred at room temperature for 16 h, then washed with 3×20 ml of water, the organic phase was dried over $Na_2SO_4$, filtered and concentrated. The residue was triturated with diethyl ether to yield 0.27 g (69%) of the title compound as crystalline material.

$^1$HNMR (400 MHz, DMSO-d6): 0.99 d (3H, $H_3$-6); 1.00 t (3H, $H_3$-21); 2.23 sex (1H, H-5); 3.03 m (2H, $H_2$-20); 3.93 t (2H, $H_2$-9); 4.36 tt (1H, H-14); 6.46 t (1H, NH-19); 6.83 m (2H, H-11, H-11')

MS: m/z: $M^{·+}$=389

Example 16

N-ethyl-N-methyl-4-(4-{3-[(2R)-2-methyl-pyrrolidin-1-yl]-propoxy}-phenoxy)-piperidine-1-carboxamide hydrochloride salt To an ice-cooled solution of 0.39 g (1 mmol) of 4-(4-{3-[(2R)-2-methyl-pyrrolidin-1-yl]-propoxy}-phenoxy)-piperidine dihydrochloride salt (Example 10) in 20 ml of dichloromethane 0.35 ml (2.5 mmol) of triethylamine was added, the mixture was stirred for 10 min and 0.18 ml (1.5 mmol)

of methyl ethyl isocyanate was added dropwise. The reaction mixture was stirred at room temperature for 16 h, then washed with 3×20 ml of water, the organic phase was dried over $Na_2SO_4$, filtered and concentrated. The crude product was dissolved in 10 ml of ethyl acetate and 4 ml of ethyl acetate containing 21 w/w % of hydrogen chloride was added, the mixture was concentrated and the residue was triturated with diethyl ether to yield 0.28 g (64%) of the title compound as crystalline material.

$^1$HNMR (400 MHz, DMSO-d6): 1.06 t (3H, $H_3$-21); 1.37 d (3H, $H_3$-6); 2.73 s (3H, $H_3$-22); 4.01 t (2H, $H_2$-9); 3.11 q (2H, $H_2$-20); 4.39 tt (1H, H-14); 6.88 m (2H, H-11, H-11'); 9.60 br (1H, $NH^+$-1)

MS: m/z: $M^{·+}$=403

Example 17

Evaluation of Histamine $H_3$ Antagonists

The in vitro affinity of the compounds of the present invention for rat histamine $H_3$ receptors can be determined according to the following procedure.

Membrane Preparation

The rat histamine $H_3$ receptor membrane was prepared as previously described by Witte et al. (British Journal of Pharmacol. 1-14, 2006). Male Sprague-Dawley rats were decapitated, their brains were removed and the cortex was isolated. The obtained tissues were homogenized in Tris-EDTA buffer (50 mM Tris-HCl, pH 7.4, 5 mM EDTA, 2 aprotinin, 1 mM benzamidine, 2 µg/ml leupeptin, 1 pepstatin) by a blender homogenizer (Ultra-Turrax). The homogenate was centrifuged at 40000 g for 20 min at 4° C. The membrane pellets were further purified by repeating the above homogenization and centrifugation steps. Final membrane preparations were obtained by rehomogenizing the pellets in 1:10 ratio in Tris-EDTA buffer (50 mM Tris-HCl, pH 7.4, 5 mM EDTA). The so obtained membrane preparation was divided into aliquots, flash frozen and stored at −80° C. until use. Protein content was determined by Lowry method using bovine serum albumin (BSA) as standard.

In Vitro Binding Assay

Receptor binding assays were performed in at least 5 concentrations, with two parallel samples in each concentrations, in at least two independent experiments using the binding buffer (50 mM Tris-HCl, pH 7.4, 5 mM $MgCl_2$), rat $H_3$ membrane (140 µg protein/tube), and N-α-[Methyl-$^3$H] methylhistamine dihydrochloride (1 nM) as radioligand. Non-specific binding was determined in the presence of 10 µM thioperamide. The samples were incubated in a final volume of 0.50 ml for 30 min at 25° C. Binding reactions were terminated by rapid filtration through UniFilter® GF/B™ fiber glass filters presoaked for at least 2 h in 0.5% polyethylene imine (PEI). The filterplates were washed nine times with 0.5 ml of ice-cold washing buffer (50 mM Tris-HCl, pH 7.4, 5 mM $MgCl_2$, 10 µg/ml saponine). The filterplates were dried at 50° C. for 45 min and 40 µl of Microscint20 (Packard) scintillation cocktail was added to each well. Filters radioactivity was determined by TopCount (Packard) scintillation counter.

Data Analyses

The ligand displacement by the compounds of the present invention was determined in at least two parallel experiments. The specific radioligand binding was defined as the difference between the total binding and the non-specific binding determined in the presence of excess of unlabelled ligand or test compounds used to specifically displace the radioligand. Results were expressed as a percent inhibition of specific binding obtained in the presence of test compounds. $IC_{50}$ values were calculated from concentration-displacement curves by sigmoidal fitting using GraphPad Prism Software 4.0. Inhibition constants ($K_i$ values) were calculated using the Cheng-Prusoff equation (Cheng Y C and Prusoff W H (1973) Biochem Pharmacol 22:3099-3108).

$K_i$ Values

The affinity at rat $H_3$ receptors of compounds of the present invention is illustrated by the following table.

| Example | Structure | rH$_3$ K$_i$ |
| --- | --- | --- |
| 1 |  | + |
| 2 |  | + |
| 3 |  | ++ |

-continued

| Example | Structure | rH₃ K$_i$ |
|---|---|---|
| 4 |  | + |
| 5 |  | ++ |
| 6 |  | + |
| 7 |  | + |
| 8 |  | + |
| 9 |  | + |
| 10 |  | ++ |
| 11 |  | + |
| 12 |  | ++ |

| Example | Structure | rH$_3$ K$_i$ |
|---|---|---|
| 13 |  | ++ |
| 14 |  | ++ |
| 15 |  | ++ |
| 16 |  | ++ |

Wherein the meaning of
++ K$_i$ <10 nM
+ K$_i$ <10-50 nM

Example 18 a-f

Preparation of Pharmaceutical Compositions a) Tablets 0.01-50 w/w % of active ingredient of formula (I), 15-50 w/w % of lactose, 15-50 w/w % of potato starch, 5-15 w/w % of polyvinyl pyrrolidone, 1-5 w/w % of talc, 0.01-3 w/w % of magnesium stearate, 1-3 w/w % of colloid silicon dioxide and 2-7 w/w % of ultraamylopectin were mixed, then granulated by wet granulation and pressed to tablets.

b) Dragées, Filmcoated Tablets

The tablets made according to the method described above were coated by a layer consisting of entero- or gastrosolvent film, or of sugar and talc. The dragées were polished by a mixture of beeswax and carnuba wax.

c) Capsules 0.01-50 w/w % of active ingredient of formula (I), 1-5 w/w % of sodium lauryl sulfate, 15-50 w/w % of starch, 15-50 w/w % of lactose, 1-3 w/w % of colloid silicon dioxide and 0.01-3 w/w % of magnesium stearate were thoroughly mixed, the mixture was passed through a sieve and filled in hard gelatin capsules.

d) Suspensions

Ingredients: 0.01-15 w/w % of active ingredient of formula (I), 0.1-2 w/w % of sodium hydroxide, 0.1-3 w/w % of citric acid, 0.05-0.2 w/w % of nipagin (sodium methyl 4-hydroxybenzoate), 0.005-0.02 w/w % of nipasol, 0.01-0.5 w/w % of carbopol (polyacrilic acid), 0.1-5 w/w % of 96% ethanol, 0.1-1 w/w % of flavoring agent, 20-70 w/w % of sorbitol (70% aqueous solution) and 30-50 w/w % of distilled water.

To solution of nipagin and citric acid in 20 ml of distilled water, carbopol was added in small portions under vigorous stirring, and the solution was left to stand for 10-12 h. Then the sodium hydroxide in 1 ml of distilled water, the aqueous solution of sorbitol and finally the ethanolic raspberry flavor were added with stirring. To this carrier the active ingredient was added in small portions and suspended with an immersing homogenizer. Finally the suspension was filled up to the desired final volume with distilled water and the suspension syrup was passed through a colloid milling equipment.

e) Suppositories

For each suppository 0.01-15 w/w % of active ingredient of formula (I) and 1-20 w/w % of lactose were thoroughly mixed, then 50-95 w/w % of adeps pro suppository (for example Witepsol 4) was melted, cooled to 35° C. and the mixture of active ingredient and lactose was mixed in it with homogenizer. The obtained mixture was mould in cooled forms.

f) Lyophilized Powder Ampoule Compositions

A 5% solution of mannitol or lactose was made with bidistilled water for injection use, and the solution was filtered so as to have sterile solution. A 0.01-5% solution of the active ingredient of formula (I) was also made with bidistilled water for injection use, and this solution was filtered so as to have sterile solution. These two solutions were mixed under aseptic conditions, filled in 1 ml portions into ampoules, the content of the ampoules was lyophilized, and the ampoules were sealed under nitrogen. The contents of the ampoules were dissolved in sterile water or 0.9% (physiological) sterile aqueous sodium chloride solution before administration.

The present invention is not to be limited in scope by the specific embodiments herein disclosed, since these embodiments are intended as illustrations of several aspects of the invention. Any equivalent embodiments are intended to be within the scope of the present invention. Indeed, various modifications of the invention in addition to those shown and described herein will become apparent to those skilled in the art from the foregoing description. Such modifications are also intended to fall within the scope of the present invention.

Example 19

Evaluation of Simultaneously Administered Histamine H3 Antagonists and Acetylcholinesterase Inhibitors Prefrontal cortex and hippocampus, the two brain regions play important roles in cognition processes. Both histamine (HA) and acetylcholine (ACh) are transmitters playing important roles in cognition. The hypofunction of the central cholinergic and histaminergic systems is considered one of the pathogenic causes of the cognitive deficits characterizing dementias. Alterations in the extracellular levels of HA and ACh were investigated after single and simultaneous treatment with histamine H3 antagonists and acetylcholine esterase inhibitors (AChEIs) in the prefrontal cortex and hippocampus of conscious, freely moving male Wistar rats (4-6 animals/group) by cerebral microdialysis technique.

Microdialysis probes were implanted in the medial prefrontal cortex (MPFC) and hippocampus (HC), and perfused with artificial AChEI-free cerebrospinal fluid (aCSF). Compounds examined in the present study were administered in 1% hydroxypropyl-methylcellulose (HPMC) and 5% polyoxiethelen(8)-sorbitane-monooleat (Tween 80) into the stomach via surgically implanted catheter.

Thirty-min samples were collected and the temporal changes in the extracellular ACh and histamine HA were followed by high-sensitivity and selectivity liquid chromatography coupled with mass spectrometry/mass spectrometry (LC-MS/MS) analytical method.

Neurotransmitter levels were expressed in percent changes relative to the basal levels obtained before drug treatment, and the effects were given as area over the baseline curves (AOBC).

Statistical evaluation of the results was performed by ANOVA/post hoc Duncan test.

Results

Treatment with H3 antagonist resulted in clear-cut increase in extracellular HA levels in both MPFC and HC whereas they produced only a modest enhancement in the ACh release. On the other hand, unequivocal increase of extracellular levels of ACh in both regions was demonstrated after AChE inhibitors. This result shows good agreement with published data with AChEIs (Cerbai et al., Eur. J. Pharmacol. (2007) 572:142-150; Scali et al., J Neural Transm. (2002) 109(7-8):1067-80; Kosasa et al., Jpn. J. Pharmacol. (1999) 81:216-222)

Figure 1:
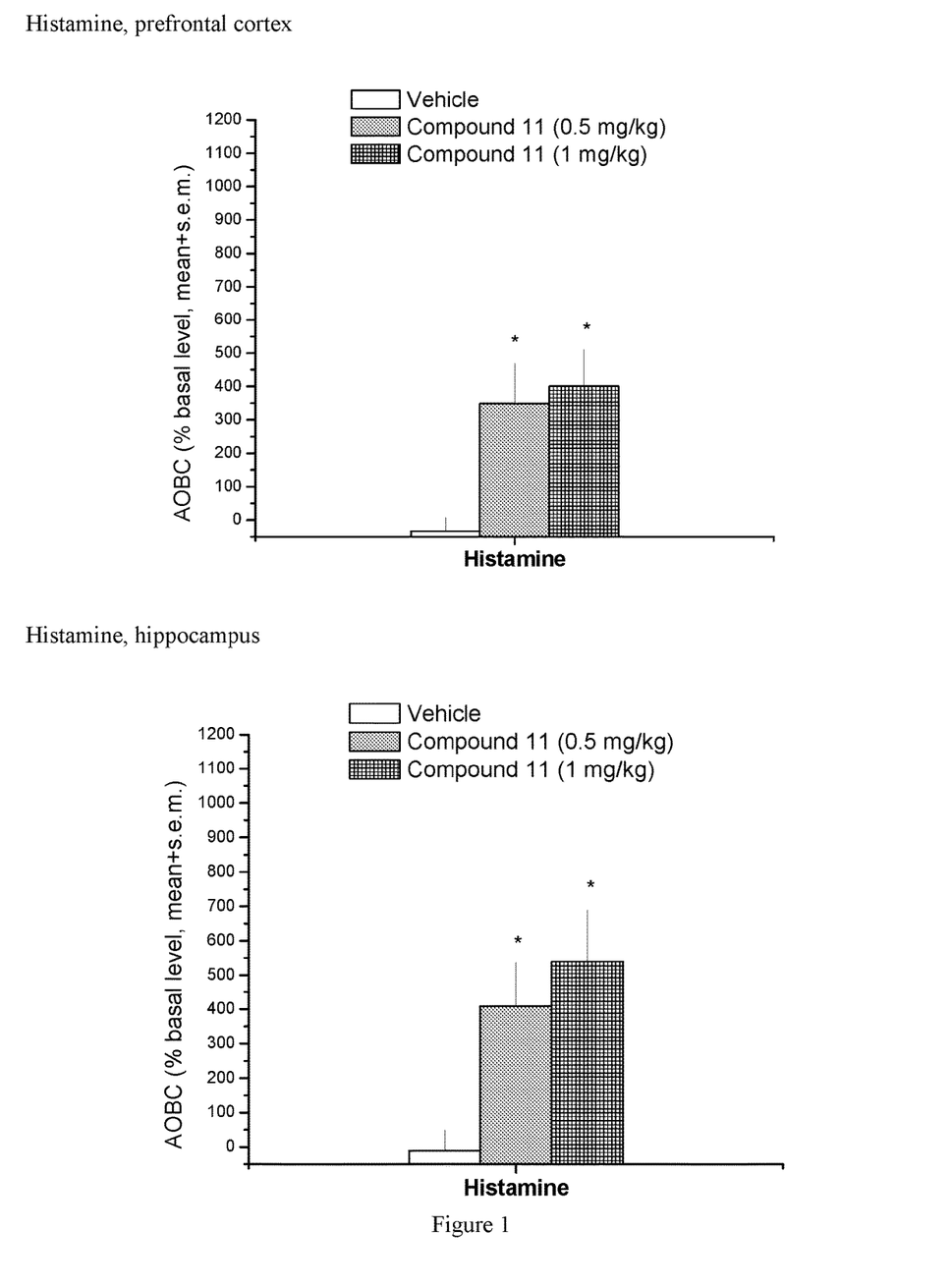
FIG. 1 shows extracellular histamine (HA) levels in the prefrontal cortex and hippocampus after treatment with H3 antagonist.
Figure 2:
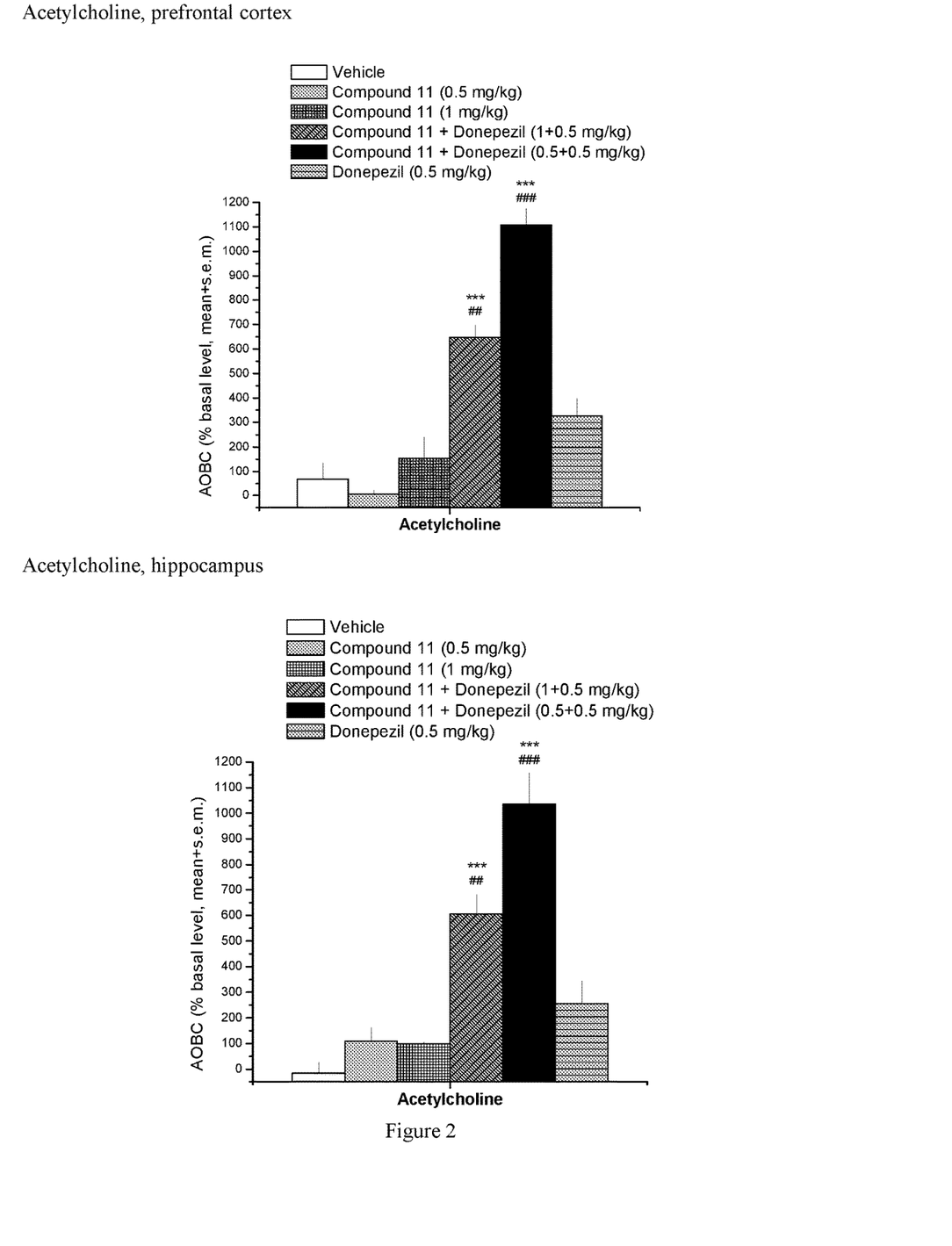
FIG. 2 shows extracellular acetylcholine (ACh) levels in the prefrontal cortex and hippocampus after treatment with H3 antagonist.

Single treatment of Compound 11 in doses of 0.5 and 1 mg/kg produced rapid and expressed increase in the extracellular HA level in both regions. (FIG. 1.). No significant changes in the ACh levels were noted after either dose. (FIG. 2.)

Surprisingly, however the AChEIs induced ACh elevation were significantly potentiated by H3 antagonists while their positive effects on HA levels was maintained. This phenomenon was found both in the prefrontal cortex and hippocampus.

For example, unequivocal and supra-additive response was noted in both regions following the simultaneous administration of donepezil, the prototype AChEI, and Compound 11. Simultaneous administration of 0.5 mg/kg donepezil and 0.5 mg/kg Compound 11 or 1 mg/kg Compound 11 resulted in supra-additive increase of extracellular ACh in both MPFC and HC. This potentiating effect was more expressed at 0.5 mg/kg dose of Compound 11 (FIG. 2) whereas the HA release evoked by Compound 11 was not changed by donepezil (data not shown).

Since there exist no pharmacokinetic interaction between the two compounds (i.e. plasma and brain levels of donepezil and Compound 11 did not change after either single or simultaneous administration, the observed potentiation of ACh levels is unexpected and is attributed to the beneficial pharmacodynamic coincidence of AChE inhibition and H3 receptor antagonism.

These results indicate that compounds with histamine H3 antagonism may possess useful and effective cognitive improving action and represent a treatment option in dementias of different origin either alone (significant HA and slight ACh increase) or in combination with AChEIs as "add-on" therapy (supraadditive ACh increase and significant HA response).

The invention claimed is:
1. Compounds of the general formula (I)

wherein
$R^1$ and $R^2$ together with the adjacent basic nitrogen atom form a 5-6 membered, one ringed saturated heterocyclic group, which optionally contains one oxygen atom and/or sulfur atom and the heterocyclic group is optionally substituted with one or two halogen atom(s), oxo group(s), $C_1$-$C_6$ alkyl group(s) or a combination thereof;
$R^3$ represents:
—C(═O)$R^4$, —C(═O)—O$R^4$, —C(═O)—N$R^4R^5$ groups,
wherein $R^4$ and $R^5$ independently from each other represent hydrogen atom, $C_1$-$C_6$ straight or branched alkyl group, or $C_3$-$C_7$ cycloalkyl group optionally substituted with $C_1$-$C_4$ alkyl group,
and/or salts and/or stereoisomers and/or diastereomers and/or hydrates and/or solvates thereof.
2. Compounds of the general formula (I) according to claim 1 wherein $R^1$ and $R^2$ together with the adjacent nitrogen atom form an optionally substituted 5-membered heterocyclic group.
3. Compounds of the general formula (I) according to claim 1 wherein $R^1$ and $R^2$ together with the adjacent nitrogen atom form a 2-methyl-pyrrolidine ring.
4. Compounds of the general formula (I) according to claim 1 wherein $R^1$ and $R^2$ together with the adjacent nitrogen atom form a 2-(R)-methyl-pyrrolidine ring.
5. Compounds of the general formula (I) according to claim 1 wherein the meaning of $R^3$ is —C(═O)$R^4$, wherein the meaning of $R^4$ is $C_1$-$C_6$ straight or branched alkyl group, or $C_3$-$C_7$ cycloalkyl group optionally substituted with $C_1$-$C_4$ alkyl group.

6. A compound of claim 1 selected from the group consisting of
4-{4-[3-(piperidin-1-yl)-propoxy]-phenoxy}-piperidine-1-carboxylic acid tert-butyl ester,
1-(4-{4-[3-(piperidin-1-yl)-propoxy]-phenoxy}-piperidin-1-yl)-ethanone hydrochloride salt,
cyclobutyl-(4-{4-[3-(piperidin-1-yl)-propoxy]-phenoxy}-piperidin-1-yl)-methanone hydrochloride salt,
(1-methyl-cyclopropyl)-(4-{4-[3-(piperidin-1-yl)-propoxy]-phenoxy}-piperidin-1-yl)-methanone hydrochloride salt,
ethyl-4-{4-[3-(piperidin-1-yl)-propoxy]-phenoxy}-piperidine-1-carboxylate hydrochloride salt,
N-ethyl-4-{4-[3-(piperidin-1-yl)-propoxy]-phenoxy}-piperidine-1-carboxamide,
N-ethyl-N-methyl-4-{4-[3-(piperidin-1-yl)-propoxy]-phenoxy}-piperidine-1-carboxamide hydrochloride salt,
4-(4-{3-[(2R)-2-methyl-pyrrolidin-1-yl]-propoxy}-phenoxy)-piperidine-1-carboxylic acid tert-butyl ester,
4-(4-{3-[(2R)-2-methyl-pyrrolidin-1-yl]-propoxy}-phenoxy)-piperidine dihydrochloride salt,
1-[4-(4-{3-[(2R)-2-methyl-pyrrolidin-1-yl]-propoxy}-phenoxy)-piperidin-1-yl]-ethanone hydrochloride salt,
cyclobutyl-[4-(4-{3-[(2R)-2-methyl-pyrrolidin-1-yl]-propoxy}-phenoxy)-piperidin-1-yl]-methanone hydrochloride salt,
(1-methyl-cyclopropyl)-[4-(4-{3-[(2R)-2-methyl-pyrrolidin-1-yl]-propoxy}-phenoxy)-piperidin-1-yl]-methanone hydrochloride salt,
ethyl-4-(4-{3-[(2R)-2-methyl-pyrrolidin-1-yl]-propoxy}-phenoxy)-piperidine-1-carboxilate hydrochloride salt,
N-ethyl-4-(4-{3-[(2R)-2-methyl-pyrrolidin-1-yl]-propoxy}-phenoxy)-piperidine-1-carboxamide and
N-ethyl-N-methyl-4-(4-{3-[(2R)-2-methyl-pyrrolidin-1-yl]-propoxy}-phenoxy)-piperidine-1-carboxamide hydrochloride salt.

7. A pharmaceutical composition comprising a therapeutically effective amount of a compound of the general formula (I) as claimed in claim 1 and/or geometric isomers and/or stereoisomers and/or diastereomers and/or salts and/or hydrates and/or solvates thereof as active ingredient.

8. Method of treating a condition which requires modulation of histamine $H_3$ receptor characterized by administering an effective amount of a compound of the general formula (I) as claimed in claim 1 and/or geometric isomers and/or stereoisomers and/or diastercomers and/or salts and/or hydrates and/or solvates thereof to a subject in need wherein said condition is selected from the group consisting of cognitive dysfunctions due to Alzheimer's disease, attention-deficit hyperactivity disorder (ADHD), narcolepsy, obesity and schizophrenia,
wherein said condition would be alleviated by modulation of histamine $H_3$ functions.

9. Combination of a compound of the general formula (I) according to claim 1 and an acetylcholinesterase inhibitor.

10. A pharmaceutical composition comprising a compound of the general formula (I) as claimed in claim 1 and an acetylcholinesterase inhibitor.

11. A pharmaceutical composition according to claim 10 wherein
$R^1$ and $R^2$ together with the adjacent nitrogen atom form an optionally substituted 5-membered heterocyclic group,
a 2-methyl-pyrrolidine ring, or
a 2-(R)-methyl-pyrrolidine ring,
and wherein $R^3$ is $C(=O)R^4$, wherein $R^4$ is $C_1$-$C_6$ straight or branched alkyl group, or $C_3$-$C_7$ cycloalkyl group optionally substituted with $C_1$-$C_4$ alkyl group.

12. A pharmaceutical composition according to claim 10 wherein the acetylcholinesterase inhibitor is donepezil, rivastigmine, galantamine or tacrine.

13. Method of treating a condition which requires modulation of histamine $H_3$ receptors and the cholinergic system characterized by administering an effective amount of a combination as claimed in claim 9 to a subject in need,
wherein said condition is selected from the group consisting of cognitive dysfunctions due to Alzheimer's disease, attention-deficit hyperactivity disorder (ADHD), narcolepsy, obesity and schizophrenia,
wherein said condition would be alleviated by modulation of histamine $H_3$ functions.

14. Method of treating a condition which requires modulation of histamine $H_3$ receptor and the cholinergic system characterized by administering an effective amount of a pharmaceutical composition according to claim 10 to a subject in need,
wherein said condition is selected from the group consisting of cognitive dysfunctions due to Alzheimer's disease, attention-deficit hyperactivity disorder (ADHD), narcolepsy, obesity and schizophrenia,
wherein said condition would be alleviated by modulation of histamine $H_3$ functions.

15. A compound of claim 1 of the following formula and/or stereoisomer and/or diastereomer and/or salt and/or hydrate and/or solvate thereof.

16. A method of modulating a histamine $H_3$ receptor, said method comprising administering an effective amount of a compound of the general formula (I) as claimed in claim 1 and/or geometric isomer and/or stereoisomer and/or diastereomer and/or salt and/or hydrate and/or solvate thereof to a mammal.

* * * * *